United States Patent [19]

Sadaki et al.

[11] Patent Number: 4,563,534

[45] Date of Patent: Jan. 7, 1986

[54] PROCESS FOR PRODUCING -2-(2-AMINOTHIAZOL-4-YL)GLYOXYLIC ACID DERIVATIVE OR A SALT THEREOF, AND INTERMEDIATES THEREFOR AND PROCESS FOR PRODUCING THE INTERMEDIATES

[75] Inventors: Hiroshi Sadaki; Hiroyuki Imaizumi; Kenji Takeda, all of Toyama; Takihiro Inaba, Namerikawa; Ryuko Takeno, Toyama; Seishi Morita, Toyama; Tetsuya Kajita, Toyama; Isamu Saikawa, Toyama, all of Japan

[73] Assignee: Toyama Chemical Co., Ltd., Tokyo, Japan

[21] Appl. No.: 504,317

[22] Filed: Jun. 14, 1983

[30] Foreign Application Priority Data

Jun. 17, 1982 [JP] Japan ................................ 57-103108
Jun. 17, 1982 [JP] Japan ................................ 57-103109
May 6, 1983 [JP] Japan ................................ 57-78201

[51] Int. Cl.$^4$ .................. C07D 277/40; C07D 277/46
[52] U.S. Cl. ...................................................... 548/194
[58] Field of Search ........................................ 548/194

[56] References Cited

U.S. PATENT DOCUMENTS 4,425,340 1/1984 Teraji ................................ 424/246

OTHER PUBLICATIONS

Major et al., J. Org. Chem. 23, 1563, (1958).
Saldabol et al., Zh. Org. Khim 14, 1910, (1978).

*Primary Examiner*—Robert Gerstl
*Attorney, Agent, or Firm*—Oblon, Fisher, Spivak, McClelland & Maier

[57] ABSTRACT

This invention relates to a novel process for producing a 2-(2-aminothiazol-4-yl)glyoxylic acid derivative or a salt thereof which are useful in producing a cephalosporin antibiotic, and to intermediates for said derivative and salt and a process for producing the intermediates.

6 Claims, No Drawings

PROCESS FOR PRODUCING 2-(2-AMINOTHIAZOL-4-YL)GLYOXYLIC ACID DERIVATIVE OR A SALT THEREOF, AND INTERMEDIATES THEREFOR AND PROCESS FOR PRODUCING THE INTERMEDIATES

This invention relates to a novel process for producing a 2-(2-(aminothiazol-4-yl)glyoxylic acid derivative or a salt thereof, and to an intermediate therefor, and a process for producing the intermediate.

2-(2-Aminothaizol-4-yl)glyoxylic acid derivative represented by the general formula or salts thereof:

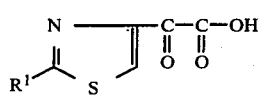
(I)

wherein $R^1$ is an amino group which may be protected, are useful starting materials for producing various cephalosporin antibiotics, and as processes for producing said starting compounds, there have heretofore been known (1) a process by which an ester of 2-[2-(protected or unprotected)aminothiazol-4-yl] acetic acid is oxidized with selenium dioxide or potassium permanganate (Japanese Patent Application Kokai (Laid-Open) No. 125,190/77 or 5,193/78) and (2) a process by which an ester of acetylglyoxylic acid is halogenated, the resulting halogenation product is reacted with thiourea, and then the reaction product is hydrolyzed (Japanese Patent Application Kokai (Laid-Open) Nos. 112,895/78 and 154,785/79).

Under such circumstances, in order to find a novel process for producing a compound represented by the general formula (I) or a salt thereof, the present inventors have conducted extensive research. As a result, they have found a novel production process, which is described hereinafter, and moreover a novel intermediate used in said production process and a process for producing the same.

An object of this invention is to provide a novel process for producing a 2-(2-aminothiazol-4-yl)glyoxylic acid derivative represented by the general formula (I) or a salt thereof.

Another object of this invention is to provide a novel intermediate for use in said production process (a compound represented by the general formula (VI) or a compound represented by the general formula (VIII) or a salt thereof, which are hereinafter described.

A further object is to provide a process for producing the intermediate.

Other objects and advantages of this invention will become apparent from the following description.

This invention will be explained below in detail.

This invention relates to a novel process for producing 2-(2-aminothiazol-4-yl)glyoxylic acid derivative represented by the general formula (I) or a salt thereof through the following production route:

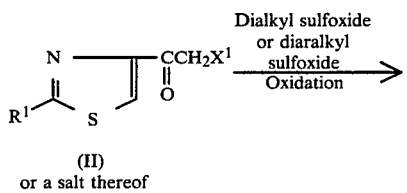

(II)
or a salt thereof

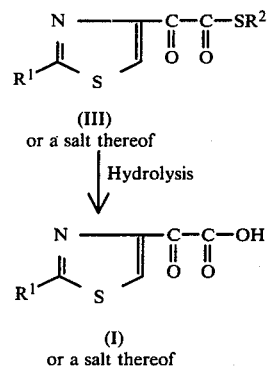

(III)
or a salt thereof

↓ Hydrolysis (I)
or a salt thereof wherein $R^1$ is as defined above; $X^1$ is a halogen atom; and $R^2$ is an alkyl group or an aralkyl group.

Protecting groups for the amino group of $R^1$ include all groups which can usually be used as aminoprotecting groups, and there may be specifically used, for example, easily removable acyl groups such as trichloroethoxycarbonyl, tribromoethoxycarbonyl, benzyloxycarbonyl, p-toluenesulfonyl, p-nitrobenzyloxycarbonyl, o-bromobenzyloxycarbonyl, (mono-, di-, tri-)chloroacetyl, trifluoroacetyl, formyl, tert.-amyloxycarbonyl, tert.-butoxycarbonyl, p-methoxybenzyloxycarbonyl, 3,4-methoxybenzyloxycarbonyl, 4-(phenylazo)benzyloxycarbonyl, 4-(4-methoxyphenylazo)benzyloxycarbonyl, (pyridine-1-oxide-2-yl)methoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl and the like. Further, there may be used other easily removable groups such as trityl, o-nitrophenylsulfenyl, 2,4-dinitrophenylsulfenyl, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene, (di-, tri-)alkylsilyl groups and the like.

As the halogen atom for $X^1$, there may be used, for example, a fluorine atom, a chlorine atom, a bromine atom, an iodine atom and the like.

As the alkyl group for $R^2$, there may be used, for example, lower alkyl groups such as methyl, ethyl, n-propyl and the like, and as the aralkyl group for $R^2$, there may be used, for example, ar-lower-alkyl groups such as a benzyl group and the like.

The salt of the compound represented by the general formula (I) includes salts at the amino group or salts at the carboxyl group. As the salts at the amino group, there may be used, for example, salts with a mineral acid such as hydrochloric acid, hydrobromic acid, hydrofluoric acid, sulfuric acid or the like; salts with an organic carboxylic acid such as oxalic acid, formic acid, trichloroacetic acid, trifluoroacetic acid or the like; or salts with a sulfonic acid such as methanesulfonic acid, p-toluenesulfonic acid, 1- or 2-naphthalenesulfonic acid or the like. As the salts at the carboxyl group, there may be used, for example, salts with an alkali metal atom such as sodium, potassium or the like or salts with an alkaline earth metal atom such as calcium, magnesium or the like.

The term "salt of the compound represented by the general formulas (II) or (III)" means a salt at the amino group in the formula (II) or (III), and includes specifically the same salts as those mentioned as the salts at the amino group of the compound represented by the general formula (I).

The reaction for obtaining a compound represented by the general formula (III) or a salt thereof from a compound represented by the general formula (II) or a salt thereof is effected by reacting the compound represented by the general formula (II) or the salt thereof with a dialkyl sulfoxide such as dimethyl sulfoxide, diethyl sulfoxide, di-n-propyl sulfoxide or the like or with a diaralkyl sulfoxide such as dibenzyl sulfoxide or the like in a solvent inert to the reaction, for example, an alcohol such as methanol, ethanol, isopropanol or the like, an ether such as tetrahydrofuran, dioxane or the like, an amide such as N,N-dimethylformamide, N,N-dimethylacetamide, hexamethyl phosphoramide or the like, or a mixed solvent thereof. The dialkyl sulfoxide or the diaralkyl sulfoxide is preferably used in an amount of 2.0 moles or more, more preferably 3.0 to 4.0 moles, per mole of the compound represented by the general formula (II) or the salt thereof, and, if necessary, it may be used as a solvent. When using a compound represented by the general formula (II) in which $X^1$ is a chlorine atom, or a salt thereof, it is preferable to effect the reaction in the presence of a bromide such as hydrogen bromide, potassium bromide, ammonium bromide, triethylammonium bromide or the like, and the amount of the bromide used in this reaction is preferably 0.5 mole or more, more preferably 0.5 to 1.0 mole, per mole of the compound represented by the general formula (II) or the salt thereof. The reaction is completed usually in 5 minutes to 20 hours at a reaction temperature of 10° to 80° C. The reaction is accelerated by adding a dialkyl sulfide such as dimethyl sulfide, diethyl sulfide or the like, a dialkyl disulfide such as dimethyl disulfide, diethyl disulfide or the like, a diaralkyl sulfide such as dibenzyl sulfide or the like, a diaralkyl disulfide such as dibenzyl disulfide or the like, an alkyl mercaptan such as methyl mercaptan, ethyl mercaptan or the like, or an aralkyl mercaptan such as benzyl mercaptan or the like in an amount of 1.0 mole or more per mole of the compound represented by the general formula (II) or the salt thereof.

By subjecting to usual hydrolysis the thus obtained compound represented by the general formula (III) or a salt thereof, it can be converted into a compound represented by the general formula (I) or a salt thereof which are useful in producing a cephalosporin compound. The hydrolysis in this case is effected in water or an alcohol such as methanol, ethanol or the like, preferably in the presence of a base. As the bases, there may be used, for example, inorganic bases such as sodium hydroxide, potassium hydroxide, barium hydroxide, calcium hydroxide, sodium carbonate, potassium carbonate and the like, or organic bases such as triethylamine, pyridine and the like. These bases are used in an amount of 2.0 moles or more per mole of the compound represented by the general formula (III) or the salt thereof.

The compounds represented by the general formulas (I), (II) and (III) or salts thereof form adducts with various solvents, and all the adducts are included in this invention.

A compound represented by the general formula (II) or a salt thereof can be produced in the following manner:

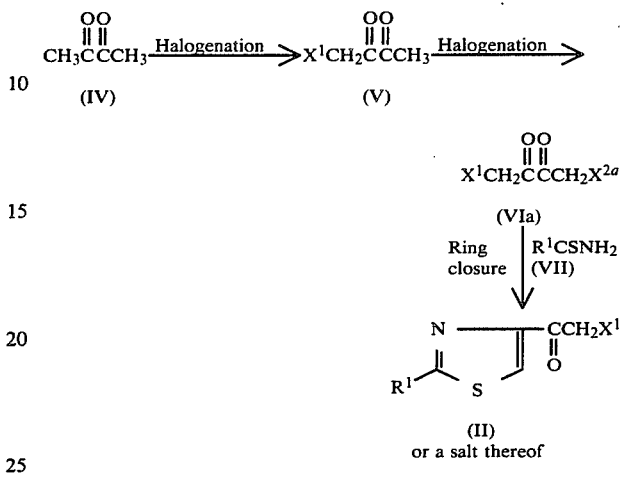

wherein $X^1$ and $X^{2a}$, which may be the same or different, are halogen atoms, and $R^1$ is as defined above.

$X^{2a}$ in the general formula (VIa) represents a halogen atom such as a fluorine atom, a chlorine atom, a bromine atom, an iodine atom or the like.

The halogenation for obtaining a 1-halogenobutane-2,3-dione represented by the general formula (V) from butane-2,3-dione represented by the formula (IV) and the halogenation for obtaining a 1,4-dihalogenobutane-2,3-dione represented by the general formula (VIa) from a 1-halogenobutane-2,3-dione represented by the general formula (V) are effected under the same conditions. For example, they are effected in the absence of a solvent or in the presence of a solvent inert to the reactions, e.g., an aromatic hydrocarbon such as benzene, toluene, xylene or the like, an ether such as diethyl ether, diisopropyl ether, tetrahydrofuran, dioxane or the like, a halogenated hydrocarbon such as methylene chloride, chloroform, carbon tetrachloride, dichloroethane or the like, a carboxylic acid such as acetic acid or the like, or a mixed solvent thereof. As the halogenating agent, there may be used a halogenating agent which is usually employed for halogenating a paraffin. For example, as chlorinating agents, there may be used chlorine, sulfuryl chloride, N-chlorosuccinimide, N-chlorophthalimide and the like, and as brominating agents, there may be used bromine, sulfuryl bromide, N-bromosuccinimide, N-bromophthalimide and the like. The amount of the halogenating agent used is preferably about equimolar to the compound represented by the formula (IV) or the general formula (V). Although the reaction conditions may vary depending on the kinds of halogenating agents to be used and the like, reaction is usually effected at a temperature of 10° C. to the reflux temperature of the solvent for a period of 30 minutes to 10 hours.

When a compound of the general formula (VIa) in which $X^1$ and $X^{2a}$ are the same halogen atoms is produced, dihalogenation may be effected in one step by directly reacting a halogenating agent with a compound represented by the formula (IV), in an amount of about 2 moles per mole of said compound. The reaction conditions in this case are the same as mentioned above.

Preferable halogenations are reactions in which the compound represented by the formula (IV) is first chlorinated with sulfuryl chloride to obtain a compound represented by the general formula (V) wherein $X^1$ is a chlorine atom, which is then brominated with bromine to obtain a compound represented by the general formula (VIa) wherein $X^{2a}$ is a bromine atom.

Subsequently, in order to obtain a compound represented by the general formula (II) or a salt thereof by reacting a 1,4-dihalogenobutane-2,3-dione, for instance, 1-bromo-4-chlorobutane-2,3-dione with a thiourea represented by the general formula (VII), the reaction is effected in the presence of a solvent inert to the reaction, for example, an alcohol such as methanol, ethanol, isopropanol or the like, an ether such as tetrahydrofuran, dioxane or the like, an amide such as N,N-dimethylformamide, N,N-dimethylacetamide, hexamethyl phosphoramide or the like, or a mixed solvent thereof or a mixed solvent of one or more of them and water. The amount of the thiourea of the general formula (VII) used may be 0.90 mole or more per mole of the compound of the general formula (VIa), and is particularly preferably 0.95 to 1.00 mole per mole of said compound. This ring closure reaction is completed usually in 5 minutes to 20 hours at a reaction temperature of $-50°$ to $10°$ C.

Further, the present invention relates also to a compound represented by the general formula (VI) or (VIII) shown below or a salt of the compound of the general formula (VIII), said compound or salt being a novel and useful intermediate, and to a process for producing the same: a 1,4-dihalogenobutane-2,3-dione represented by the general formula:

$$X^1CH_2\overset{O}{\overset{\|}{C}}\overset{O}{\overset{\|}{C}}CH_2X^2 \quad (VI)$$

wherein $X^1$ and $X^2$ represent different halogen atoms, a 2-aminothiazole derivative represented by the general formula or a salt thereof:

(VIII)

wherein $R^1$ is as defined above and $R^3$ is a monohalogenomethyl, an alkylthiocarbonyl or an aralkylthiocarbonyl group.

The compounds represented by the general formulas (VI) and (VIII) and salts of the compounds of the general formula (VIII) are obtained by the process described above.

The compound represented by the general formula (VIII) or the salt thereof includes the above-mentioned compounds represented by the general formulas (II) and (III) or salts thereof.

As the monohalogenomethyl group in $R^3$, there may be used, for example, a chloromethyl group, a bromomethyl group, an iodomethyl group and the like; as the alkylthiocarbonyl group, there may be used, for example, a methylthiocarbonyl group, an ethylthiocarbonyl group, a n-propylthiocarbonyl group and the like; and as the aralkylthiocarbonyl group, there may be used, for example, a benzylthiocarbonyl group and the like.

Among the compounds of the general formula (VIII), particularly preferable are compounds in which $R^1$ is an amino group or a formylamino group and $R^3$ is a chloromethyl group or a methylthiocarbonyl group.

With respect to the

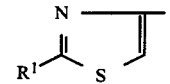

group in each of the above-mentioned general formulas, tautomers exist as shown in the following equilibrium formulas and the tautomers also are included in this invention:

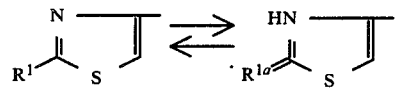

wherein $R^{1a}$ is an imino group which may be protected, and $R^1$ is as defined above.

As the protecting group for the imino group in $R^{1a}$, there may be used the monovalent aminoprotecting groups explained in the case of $R^1$. The present invention is explained below referring to Examples, which are not by way of limitation but by way of illustration.

EXAMPLE 1

(1) To a mixed solution of 172 g of butane-2,3-dione and 172 ml of benzene was added dropwise 163 ml of sulfuryl chloride with stirring at 60° C. over a period of 3 hours. After completion of the addition, the thus obtained reaction mixture was stirred at said temperature for 1 hour and then under reflux for 1 hour, and thereafter rectified under reduced pressure to obtain 124 g (51.5% yield) of 1-chlorobutane-2,3-dione having a boiling point of 53.5° to 55.0° C./14 mmHg.

IR(neat)cm$^{-1}$:$\nu_{C=O}$1720

NMR(CDCl$_3$)$\delta$values:

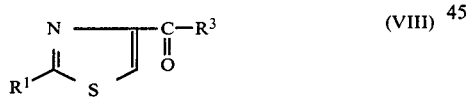

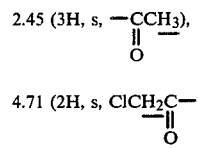

(2) To a mixed solution of 120.5 g of 1-chlorobutane-2,3-dione and 120 ml of dichloroethane was added dropwise 160 g of bromine with stirring under reflux over a period of 2 hours. After completion of the addition, the thus obtained reaction mixture was further stirred under reflux for 30 minutes, and then cooled to 20° C. The deposited crystals were collected by filtration, washed with dichloroethane, and then dried to obtain 109 g (54.6% yield) of 1-bromo-4-chlorobutane-2,3-dione having a melting point of 120° to 121.5° C.

IR(KBr)cm$^-$:$\nu_{C=O}$1760,1735

NMR(CD$_3$OD)$\delta$values: 3.70 (1H, s), 3.83 (1H, s), 4.63 (1H, s), 4.81 (1H, s). (3) A suspension consisting of 20.0 g of 1-bromo-4-chlorobutane-2,3-dione and 140 ml of ethanol was cooled to $-35°$ C., and 7.3 g of thiourea was added with stirring. The resulting reaction solution was stirred at said temperature for 4 hours, and the temperature of the solution was raised to $-20°$ C. over a period of 30 minutes, after which the solution was further stirred at said temperature for 2 hours. Thereafter, the temperature of the reaction solution was raised to 10° C. over a period of 1 hour and 30 minutes to deposit white crystals. The crystals were collected by filtration, washed with ethanol, and then dried to obtain 24.9 g (81.8% yield) of 1:1 solvate of ethanol and the hydrobromide salt of 2-amino-4-chloroacetylthiazole having a melting point of 191° C. (decomp.).

IR(KBr)cm$^{-1}$:$\nu_{C=O}$1695
NMR(d$_6$-DMSO)δvalues:

1.09 (3H, t, J = 7.5Hz, C$\underline{H_3}$CH$_2$OH), 3.54 (2H, q, J = 7.5Hz, CH$_3$C$\underline{H_2}$OH), 5.17 (2H, s, —CC$\underline{H_2}$Cl),
        ‖
        O 8.40 (4H, bs, 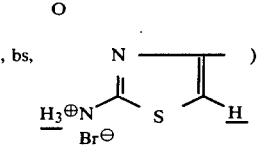 )

EXAMPLE 2

A mixed solution of 30.4 g of 1:1 solvate of ethanol and hydrobromide salt of 2-amino-4-chloroacetylthiazole, 91 ml of dimethyl sulfoxide and 11.9 g of potassium bromide was heated to 30° C., and 8.9 ml of dimethyl disulfide was added. The resulting reaction mixture was stirred at 30° to 35° C. for 2 hours, and then poured into 300 ml of ice water.

Subsequently, the resulting mixture was adjusted to pH 5.5 with sodium hydrogencarbonate. The deposited solid was collected by filtration and dissolved in 80 ml of 1 N hydrochloric acid, and a small amount of the insoluble material was removed therefrom by filtration, after which the filtrate was adjusted to pH 5.5 with sodium hydrogencarbonate. The deposited crystals were collected by filtration, washed with water, and then dried to obtain 11.7 g (61.4% yield) of 2-(2-aminothiazol-4-yl)thioglyoxylic S-acid methyl ester having a melting point of 130° C. (decomp.).

IR(KBr)cm$^{-1}$:$\nu_{C=O}$1675,1650
NMR(d$_6$-DMSO)δvalues:

2.45 (3H, s, —CSCH$_3$),
        ‖
        O 7.60 (2H, bs, H$_2$N—), 8.24 (1H, s, 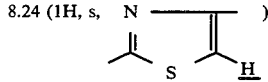 )

EXAMPLE 3

To 10.1 g of 2-(2-aminothiazol-4-yl)thioglyoxylic S-acid methyl ester and 80 ml of water was added 10.6 g of sodium carbonate with ice-cooling, and the resulting mixture was stirred at the same temperature for 1 hour. Subsequently, the thus obtained reaction mixture was adjusted to pH 2.5 with 6 N hydrochloric acid at the same temperature. The deposited crystals were collected by filtration, washed with water, and then dried to obtain 6.2 g (67.8% yield) of 2-(2-aminothiazol-4-yl)glyoxylic acid having a melting point of above 200° C.

IR(KBR)cm$^{-1}$:$\nu_{C=O}$1660
NMR(d$_6$-DMSO)δvalues:

8.11 (1H, s, 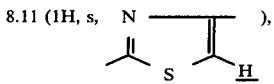 ), 7.50–8.30 (2H, bs, 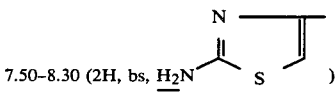 )

EXAMPLE 4

A mixture of 40.8 g of acetic anhydride and 8.4 g of formic acid was stirred at 40° to 45° C. for 1 hour. To the resulting mixture was added 20.2 g of 2-(2-aminothiazol-4-yl)thioglyoxylic S-acid metyl ester, with water-cooling, after which the resulting mixture was stirred at 25° C. for 1 hour. Subsequently, 60 ml of water was added dropwise to the thus obtained reaction mixture with ice-cooling, after which the resulting mixture was stirred with water-cooling for 30 minutes, and the deposited crystals were collected by filtration. The crystals were washed successively with water and acetone and then dried to obtain 21.9 g (94.4% yield) of 2-(2-formylaminothiazol-4-yl)thioglyoxylic S-acid methyl ester having a melting point of above 230° C.

IR(KBr)cm$^{-1}$:$\nu_{C=O}$1690,1670,1650

EXAMPLE 5

In 50 ml of water was suspended 7.8 g of 1:1 solvate of ethanol and hydrobromide salt of 2-amino-4-chloroacetylthiazole, and to the suspension was gradually added 2.3 g of sodium hydrogencarbonate at 20° C. with stirring over a period of 15 minutes. The deposited crystals were collected by filtration, washed with 10 ml of water, and then dried to obtain 4.5 g (98.8% yield) of 2-amino-4-chloroacetylthiazole having a melting point of 147° C. (decomp.).

IR(KBr)cm$^{-1}$:$\nu_{C=O}$1675,1600
NMR(d$_6$-DMSO)δvalues:

5.00 (2H, s, —CC$\underline{H_2}$Cl),
        ‖
        O 7.47 (2H, bs, 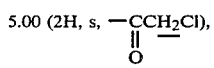), 7.80 (1H, s, 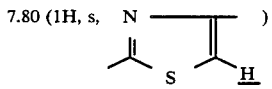 )

EXAMPLE 6

(1) In 200 ml of water is suspended 23 g of 2-(2-formylaminothiazol-4-yl)thioglyoxylic S-acid methyl ester, and 125 ml of a 2 N aqueous sodium hydroxide solution was added thereto dropwise with water-cooling over a period of 30 minutes, after which the resulting mixture was stirred at room temperature for 1 hour. After completion of the reaction, the thus obtained reaction mixture was adjusted to pH 2.5 with 6 N hydrochloric acid. The deposited crystals were collected by filtration, washed successively with water and acetone, and then dried to obtain 16.2 g (81.6% yield) of 2-(2-formylaminothiazol-4-yl)glyoxylic acid having a melting point of above 210° C.

IR(KBr)cm$^{-1}$:$\nu_{C=O}$1660

NMR(d$_6$-DMSO)δvalues:

8.31 (1H, s), 8.60 (1H, s), 12.8 (1H, bs). (2) 2-(2-Formylaminothiazol-4-yl)glyoxylic acid was hydrolyzed according to a conventional method to obtain 2-(2-aminothiazol-4-yl)glyoxylic acid.

The physical properties of this compound were identical with those of the compound obtained in Example 3.

What is claimed is:

1. A process for producing (2-(2-aminothiazol-4-yl)-glyoxylic acid derivative represented by the formula I or a salt thereof:

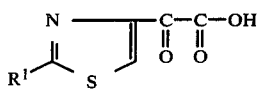

(I)

wherein R$^1$ is an amino group or protected amino group, which comprises reacting a compound represented by the formula II or a salt thereof:

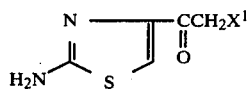

(II)

wherein X$^1$ is a halogen atom, with a di-lower alkyl sulfoxide in an amount of 2.0 moles or more, a bromide in an amount of 0.5 mole or more, and a di-lower alkyl disulfide in an amount of 1.0 mole or more, said amounts per mole of compound II, then optionally introducing the amino-protecting group to the resulting compound, and then hydrolyzing the resulting compound represented by the formula III or salt thereof:

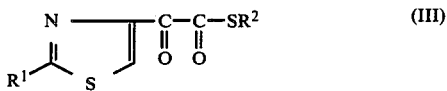

(III)

wherein R$^1$ is as defined above, and R$^2$ is a lower alkyl group, to yield the compound represented by the formula I.

2. A process according to claim 1, wherein X$^1$ is a chlorine atom.

3. A process according to claim 2, wherein the di-lower alkyl sulfoxide is dimethyl sulfoxide.

4. A process according to claim 3, wherein the bromide is a potassium bromide.

5. A process according to claim 4, wherein the di-lower alkyl disulfide is dimethyl disulfide.

6. A process according to claim 1, wherein the reaction with a di-lower alkyl sulfoxide is effected at a temperature of 10° to 80° C.

* * * * *